United States Patent
Brown et al.

(10) Patent No.: US 8,853,141 B2
(45) Date of Patent: Oct. 7, 2014

(54) SULFOMETHYLSUCCINATES, PROCESS FOR MAKING SAME AND COMPOSITIONS CONTAINING SAME

(75) Inventors: Aaron Michael Brown, Chicago, IL (US); Xue Min Dong, Lincolnshire, IL (US)

(73) Assignee: Stepan Company, Northfield, IL (US)

( * ) Notice: Subject to any disclaimer, the term of this patent is extended or adjusted under 35 U.S.C. 154(b) by 41 days.

(21) Appl. No.: 13/505,713

(22) PCT Filed: Nov. 3, 2010

(86) PCT No.: PCT/US2010/055266
§ 371 (c)(1), (2), (4) Date: Jun. 25, 2012

(87) PCT Pub. No.: WO2011/109047
PCT Pub. Date: Sep. 9, 2011

(65) Prior Publication Data
US 2012/0270764 A1    Oct. 25, 2012

Related U.S. Application Data

(60) Provisional application No. 61/280,439, filed on Nov. 3, 2009.

(51) Int. Cl.
A61Q 5/02     (2006.01)
A61K 8/46     (2006.01)
C07C 309/17   (2006.01)
C11D 1/12     (2006.01)

(52) U.S. Cl.
CPC ............... C07C 309/17 (2013.01); A61K 8/466 (2013.01); C11D 1/123 (2013.01); A61Q 5/02 (2013.01)
USPC ............ 510/130; 510/424; 510/426; 510/428

(58) Field of Classification Search
None
See application file for complete search history.

(56) References Cited

U.S. PATENT DOCUMENTS

| | | |
|---|---|---|
| 2,028,091 A | 1/1936 | Jaeger |
| 2,386,445 A | 10/1945 | Bernhard et al. |
| 3,929,678 A | 12/1975 | Laughlin et al. |
| 3,987,043 A | 10/1976 | Lamberti |
| 4,199,483 A | 4/1980 | Jones |
| 4,222,905 A | 9/1980 | Cockrell, Jr. et al. |
| 4,438,025 A | 3/1984 | Ota et al. |
| 5,015,414 A | 5/1991 | Kamegai et al. |
| 5,705,147 A | 1/1998 | Shapiro et al. |
| 5,929,022 A | 7/1999 | Velazquez |
| 2008/0058236 A1 | 3/2008 | Ospinal et al. |
| 2009/0188055 A1 | 7/2009 | Bernhardt et al. |
| 2010/0184633 A1* | 7/2010 | Bernhardt et al. ............ 510/384 |

OTHER PUBLICATIONS

Ding, *J. Surf. Det. 14* (2010) 43.
Kosswig, K., "Surfactants," section 6.2.6 re Sulfosuccinates.

* cited by examiner

*Primary Examiner* — Necholus Ogden, Jr.
(74) *Attorney, Agent, or Firm* — Dilworth IP LLC

(57) ABSTRACT

Sulfomethylsuccinates of the formula:

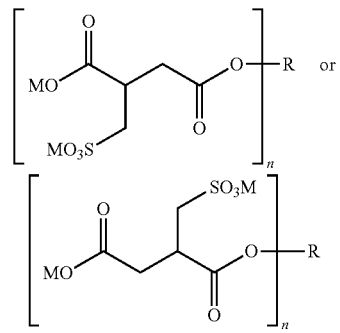

wherein R is an alkyl, alkenyl, alkynyl, alkoxylated alkyl, cycloalkyl, cycloalkenyl, cycloalkynyl, branched alkyl, branched alkenyl, branched alkynyl, branched alkoxylated alkyl, aromatic, substituted alkyl aromatic, substituted alkenyl aromatic or substituted alkoxylated aromatic group; M is a cation, hydrogen, amine or ammonium salt or combinations thereof, and each M may be the same as or different from the other; and n is from 1 to about 6. Processes for synthesizing the sulfomethylsuccinates are also provided. The sulfomethylsuccinates can be used as surfactants, emulsifiers, skin feel agents, film formers, rheological modifiers, solvents, release agents, lubrication agents, conditioners, and dispersants, etc.

8 Claims, 2 Drawing Sheets

Step 1

Step 2

Step 3

SULFOMETHYLSUCCINATES, PROCESS FOR MAKING SAME AND COMPOSITIONS CONTAINING SAME

FIELD OF THE INVENTION

The present invention relates to sulfomethylsuccinate compounds, to processes of making the sulfomethylsuccinate compounds and to compositions comprising the sulfomethylsuccinate compounds. More particularly, the present invention relates to sulfomethylsuccinate anionic surfactants that are derived from 100% renewable carbon and possess superior foaming properties, to processes of making the sulfomethylsuccinate compounds from itaconic acid and itaconic acid derivatives, and to formulated products containing the sulfomethylsuccinate compounds that may be employed in a wide variety of personal, household and industrial applications.

BACKGROUND

One of the strong trends in personal care products is toward natural (100% carbon renewable) and mild formulations. This trend is especially evident in shampoos, body washes, liquid hand soaps, foaming facial cleansers and shower gels. Currently, alkyl polyglycosides and sodium lauryl sulfate dominate the naturally derived surfactant market. Alkyl polyglycosides suffer from their cost, lack of viscosity build, low foaming, and dark color, while sodium lauryl sulfate has negative connotations regarding its irritancy. Acyl glutamates make up the remaining field of natural surfactants and are often extravagantly priced which makes them cost prohibitive for use as primary or secondary surfactants.

In the area of personal care, there is a desire for surfactants that are mild, salt-free, sulfate-free and 100% active. Other desirable attributes include being in liquid form at room temperature, having a non-nitrogen containing structure, an ability to formulate products using a cold process, and an ability to perform as good as or better than existing surfactants. For household, industrial and institutional cleaning products, both surfactants and solvents are important ingredients. Desirable attributes for such products include the ability to emulsify, suspend or penetrate greasy or oily soils and suspend or disperse particulates, in order to clean surfaces; and then prevent the soils, grease, or particulates from re-depositing on the newly cleaned surfaces. For example, an effective laundry detergent product should remove dirt from clothes and then keep the dirt in solution so that it is removed with the wash water instead of re-depositing on the washed clothes.

It is also desirable to have the ability to control the foaming of different household, industrial and institutional products depending on the desired end-use applications. For example, a liquid manual dish washing detergent preferably has the ability to foam in the presence of soil that is being removed from dishware. Yet, for a laundry detergent or automated dish washing detergent for use in a high efficiency washing machine, low foam is desired to achieve the best cleaning and to avoid excess foaming to allow machine proper operation. Other desirable properties of such consumer products include the ability to clarify the formulation and to improve stability. For hard surface cleaners, it is desirable to have the ability to wet various surface types and couple or suspend soils to leave the surface free from residue in the form of streaking and/or filming.

SUMMARY OF THE INVENTION

In one aspect, the present invention provides sulfomethylsuccinates of the formula:

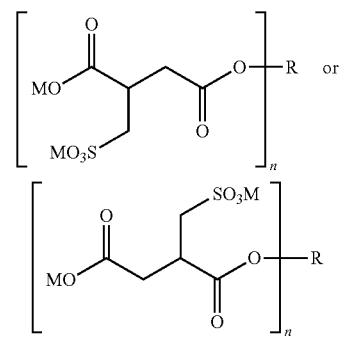

wherein R is an alkyl, alkenyl, alkynyl, alkoxylated alkyl, cycloalkyl, cycloalkenyl, cycloalkynyl, branched alkyl, branched alkenyl, branched alkynyl, branched alkoxylated alkyl, aromatic, substituted alkyl aromatic, substituted alkenyl aromatic or substituted alkoxylated aromatic group; M is a cation, hydrogen, amine or ammonium salt or combinations thereof; and n is from 1 to about 6.

In another aspect, the invention provides a process for making a sulfomethylsuccinate by:

(i) reacting itaconate anhydride with an alcohol of the general formula ROH to yield an itaconate ester, wherein R is an alkyl, alkenyl, alkynyl, alkoxylated alkyl, cycloalkyl, cycloalkenyl, cycloalkynyl, branched alkyl, branched alkenyl, branched alkynyl, branched alkoxylated alkyl, aromatic, substituted alkyl aromatic, substituted alkenyl aromatic or substituted alkoxylated aromatic group; and (ii) reacting the itaconate ester with a sulfonating agent to produce a sulfomethylsuccinate with the general formula

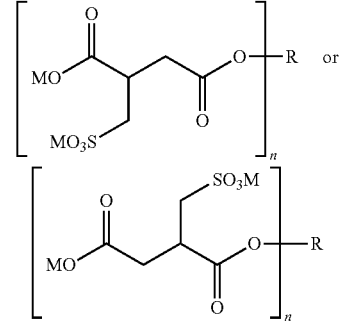

wherein M is a cation, hydrogen, amine or ammonium salt, or a combination thereof; and n is from 1 to about 6.

In another aspect, the present invention provides a composition containing a sulfomethylsuccinate of the formula:

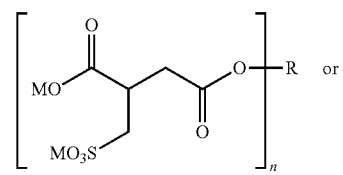

-continued

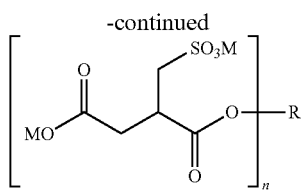

wherein R is an alkyl, alkenyl, alkynyl, alkoxylated alkyl, cycloalkyl, cycloalkenyl, cycloalkynyl, branched alkyl, branched alkenyl, branched alkynyl, branched alkoxylated alkyl, aromatic, substituted alkyl aromatic, substituted alkenyl aromatic or substituted alkoxylated aromatic group;

M is a cation, hydrogen, amine or ammonium salt or combinations thereof; and n is less than or equal to 2; and a surfactant, dye, water, solvent, fragrance, emollient, emulsifier, humectant, builder, chelator, rheology modifier, salt, pH adjuster, carrier, polymer, vitamins, amino acids, sensorial modifiers, skin wrinkle reduction agent, ultra violet absorbing agents, exfoliating agent, anti-bacterial agent, enzyme, anti-fungal agent, or preservative, or a combination thereof.

In another aspect, the invention provides a composition containing a sulfomethylsuccinate of the formula:

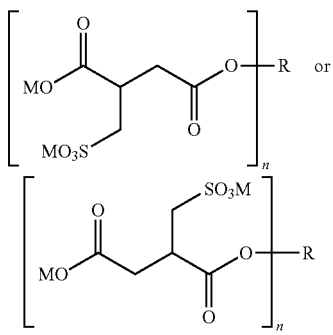

wherein R is an alkyl, alkenyl, alkynyl, alkoxylated alkyl, cycloalkyl, cycloalkenyl, cycloalkynyl, branched alkyl, branched alkenyl, branched alkynyl, branched alkoxylated alkyl, aromatic, substituted alkyl aromatic, substituted alkenyl aromatic or substituted alkoxylated aromatic group; M is a cation, hydrogen, amine or ammonium salt or a combination thereof; and n equals 1. The composition also includes one or more of a surfactant, dye, water, solvent, fragrance, emollient, emulsifier, humectant, builder, chelator, rheology modifier, salt, pH adjuster, carrier, polymer, vitamins, amino acids, sensorial modifiers, skin wrinkle reduction agent, ultra violet absorbing agents, exfoliating agent, anti-bacterial agent, enzyme, anti-fungal agent, or preservative, or a combination thereof.

According to still another aspect of the invention, a soap bar contains (a) about 0.01 to about 60% of the sulfomethylsuccinate described herein, (b) about 30% to about 95% of a C6-C22 soap; (c) about 0.5% to about 30% of a C6-C22 fatty acid; (d) about 0.1% to about 5% of an electrolyte; (e) about 0.5% to about 15% of a polyhydric alcohol; and (f) about 3% to about 22% of water. The soap bar may optionally contain up to about 50% of a synthetic surfactant; and optionally up to about 30% of at least one alpha sulfonated alkyl ester, at least one sulfonated fatty acid, or a mixture thereof, all based on the total weight of the soap bar.

In accordance with another optional embodiment of the invention, an alkyl sulfomethylsuccinate is provided which possesses the following general structure:

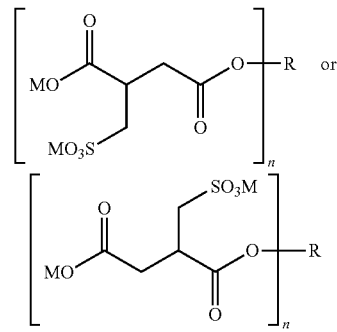

wherein R is an alkyl group or alkoxylated alkyl group, M is an alkali metal, hydrogen alkaline earth metal, amine or ammonium salts or combinations thereof and n is from 1 to about 6. In accordance with certain embodiments, R contains from 1 to about 24, alternatively from 1 to about 18, alternatively from about 6 to about 18, alternatively from about 12 to about 14, carbon atoms. R can be derived from a hydroxyl-containing compound containing from 1 to about 6 hydroxyl groups. One preferred hydroxyl-containing compound is a fatty alcohol, such as those containing from about 6 to about 18 carbon atoms. Optionally, the alkyl group in an alkyl sulfomethylsuccinate comprises from about 6 to about 18 carbon atoms, for example, from about 12 to about 14 carbon atoms, such as a lauryl/myristyl group. Optionally, M is hydrogen, lithium, sodium, potassium, beryllium, calcium, magnesium, iron ammonium, monoethanolamine, diethanolamine triethanolamine or mixtures thereof. In certain embodiments, M is sodium or hydrogen. In particular, an alkyl sulfomethylsuccinate may be a lauryl disodium sulfomethylsuccinate.

In accordance with another embodiment of the invention, at least one alkyl sulfomethylsuccinate of the present invention is an alkyl disodium sulfomethylsuccinate or alkyl sulfomethylsuccinic acid having the following general structure:

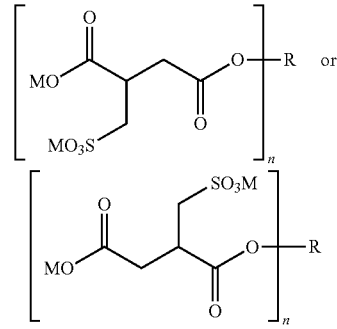

wherein R is an alkyl group or alkoxylated alkyl group and M is sodium or hydrogen or mixture thereof, and n equals 1 or 2. Optionally, the hydroxyl-containing compound used to make the alkyl sulfomethylsuccinate of the presently described invention contains at least one primary hydroxyl group.

Generally, each M in a given structure may be different from, or the same as, the other.

When the hydroxyl-containing compound contains two or more hydroxyl groups, a compound containing two or more sulfomethylsuccinate groups can be formed wherein the R group is a bridging group between the sulfomethylsuccinate groups. For example, when a compound containing two hydroxyl groups is used as the bridging molecule, the sulfomethylsuccinate can be represented by the following general structure:

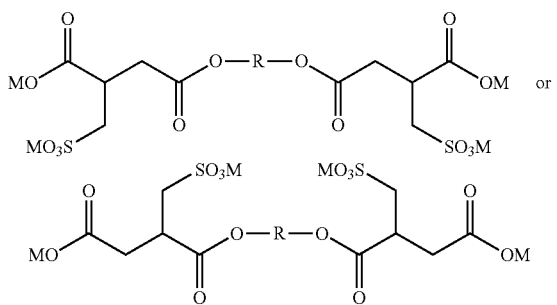

Processes for producing alkyl sulfomethylsuccinates of the invention are further provided in accordance with the teachings of the present invention. At least one process includes the steps of (i) providing an alkyl or alkoxy itaconate of the general formula

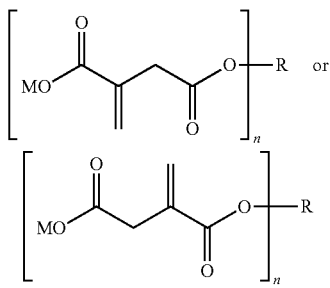

wherein R is $C_1$-$C_{24}$ alkyl and M and n are as stated above, and which may be optionally alkoxylated, and (ii) reacting the alkyl itaconate with a sulfonating agent such as alkali sulfite in water to produce the alkyl sulfomethylsuccinates of the present invention.

In accordance with another embodiment of the invention, a composition comprising at least one alkyl sulfomethylsuccinate is provided. The composition can be an aqueous system or provided in other forms.

DETAILED DESCRIPTION OF THE INVENTION

Figure 1:
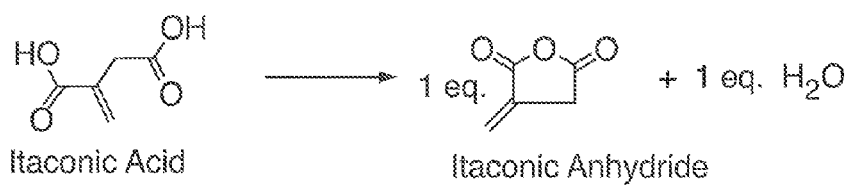
FIG. 1 is a chart showing a process for making sulfomethylsuccinates according to one aspect of the invention.
Figure 1:
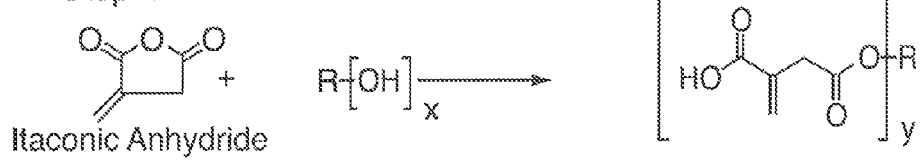
Figure 1:
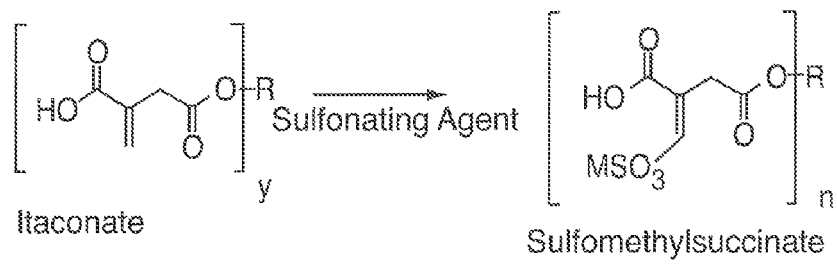

Sulfomethylsuccinates of the present invention can be produced by a process described as follows with reference to FIG. 1. As indicated by the Step 1 portion of FIG. 1, itaconic acid is dehydrated into itaconic anhydride with the release of 1 molar equivalent of water in the presence of acid catalyst and heat. The acid catalyst can be, for example, $H_2SO_4$, HCl, methane sulfonic acid, p-toluenesulfonic acid (pTSA), amberlyst 15 (acidic resin), zeolite, or a NAFION® ionomer (a sulfonated tetrafluoroethylene copolymer, CAS No. 31175-20-9, available from E.I. du Pont de Nemours and Company), or a mixture thereof. The invention is not limited in this regard, and any other catalyst effective for facilitating the dehydration of itaconic acid into itaconic anhydride can be used. In accordance with at least some embodiments, the catalyst is effective in amounts of about 1.0 wt % or less, based on the weight of itaconic anhydride in the reaction mixture, for example, about 0.01 wt % to about 0.4 wt %.

Optionally, Step 1 can be performed under vacuum and in solvent with removal of the water released upon dehydration of the itaconic acid. Suitable solvents include hexanoic acid, octanoic acid, methyl hexanoate, cyclohexanone and diproplylene glycol dimethyl ether (DPGDME), although the invention is not limited in this regard and any other suitable solvent may be used. The dehydration reaction can take place at about 100° C. to about 200° C., the temperature being selected to be suitable for the solvent used. The use of a solvent that will reflux will facilitate the removal of released water. Additionally, a trap (e.g., a Dean Stark trap) is utilized to aid in the removal of water. Methyl esters, fatty acids, glycols, ethers and traditional organic solvents may be employed in Step 1. Vacuum settings can be selected to be suitable for the solvent being used and the specific temperature targeted.

In certain embodiments, the dehydration reaction is carried out at about 130° C. to about 170° C. For example, when using DPGDME as the solvent with a target temperature of about 130° C., a suitable vacuum setting is 120 mm Hg. The solvent may be removed after the dehydration reaction, before or after esterification with an alcohol as described for Step 2.

In Step 2, the itaconic anhydride undergoes an esterification reaction with an hydroxyl-containing compound represented as R[OH]x. As used herein, the term "hydroxyl-containing compound" refers generally to a compound that contains at least one hydroxyl ("OH") group, i.e., x is at least equal to one (1). The R group of the hydroxyl-containing compound may be an alkyl, alkenyl, alkynyl, alkoxylated alkyl, cycloalkyl, cycloalkenyl, cycloalkynyl, branched alkyl, branched alkenyl, branched alkynyl, branched alkoxylated alkyl, aromatic, substituted alkyl aromatic, substituted alkenyl aromatic or substituted alkoxylated aromatic group.

In various embodiments, the R[OH]x compound may be monohydric (i.e., x=1), but the invention is not limited in this regard and in other embodiments, the R[OH]x compound may be polyhydric (i.e., x may be greater than 1). The esterification reaction (Step 2 of FIG. 1) may result in one or more itaconate groups reacting with the polyhydric R[OH]x compound, resulting in a plurality of itaconate groups on the R group. Thus, in FIG. 1, when R[OH]x is monohydric (x=1), then n=1 in the product sulfomethylsuccinate. When R[OH]x is polyhydric (x>1), the esterification (Step 2) may occur on all or fewer than all of the hydroxyl groups, so y in FIG. 1 is at least equal to one and may be equal to, or less than x. Since the sulfonation step (Step 3) may occur on all or fewer than all of the esterified itaconate groups, and accordingly, n in the product sulfomethylsuccinate is at least equal to one and may be equal to, or less than, the smaller of x and y.

In some embodiments, R is an alkyl or alkoxy group. In some embodiments where R is alkyl, no solvent is used in step 1 or 2 of the process, and the alkyl sulfomethylsuccinate produced is a clear, homogeneous liquid in water. The hydroxyl-containing compound used to make the alkyl sulfomethylsuccinates of the present invention can be straight, branched, saturated, or unsaturated, and can be derived from natural or synthetic feed stocks.

In some embodiments, the hydroxyl-containing compound is a fatty alcohol, such as those containing from about 6 to about 18 carbon atoms. Optionally, ROH is an alkoxylated fatty alcohol. In some embodiments, the hydroxyl-containing compound is a monohydric primary alcohol. In such embodiments, the esterification reaction of Step 2 may be stoichiometric, i.e., the molar ratio of itaconic anhydride to fatty alcohol may be 1:1. Optionally, the fatty alcohol is a primary fatty alcohol.

Catalyst and solvents are not required for the esterification reaction. The temperature of the reaction affects the duration of the reaction. For example, in some embodiments, the esterification is carried out at an elevated temperature of about 90° C., and the esterification reaction may take about 2 hours to substantial completion. In other embodiments, an esterification reaction may proceed rapidly at 130° C. and substantially complete conversion may be obtained in about 20 minutes. As discussed further below, various kinds of alcohols can be used in Step 2. In many embodiments, Step 2 will yield both alpha- and beta-esters, with an increase in the alpha ester associated with higher reaction temperatures. In some embodiments, beta monoesters can be obtained at about 95% purity.

After substantial completion of the esterification reaction of Step 2, a sulfonating agent, preferably a sulfitating agent, is added to the product ester and the solution stirred at a temperature and duration sufficient to yield the product sulfomethylsuccinate, in Step 3. The sulfonating agent may be an alkali sulfite ($MSO_3$), although the invention is not limited in this regard and any suitable sulfonating agent may be used. The product may include alpha- and beta-sulfomethylsuccinates in proportions that correspond to the relative proportions of alpha- and beta-esters subjected to sulfonation. Generally, each M in a sulfomethylsuccinate group n may be the same as, or different from, the other, depending on the nature of the sulfonating or sulfitating agent(s) used.

No solvent is used in some embodiments of the process, and the sulfomethylsuccinate produced is a clear, homogeneous liquid in water.

In an illustrative embodiment, once the released water is substantially removed in Step a, the itaconic anhydride undergoes an esterification reaction with lauryl alcohol, a primary fatty alcohol. At elevated temperature, e.g., about 90° C., the esterification reaction takes about 2 hours to completion. The temperature of the reaction will dictate the duration required for substantially complete reaction. Catalyst and solvents are not required. For example, at 130° C., the reaction proceeds rapidly and substantially complete conversion is obtained in about 20 minutes. This reaction is stoichiometric, i.e., the itaconic anhydride to lauryl alcohol molar ratio is 1:1. At elevated temperatures, one may see an increase in the alpha monoester product. In some embodiments, the beta monoester is formed at about 95% purity.

In step 3, upon completion of the esterification reaction, 1 molar equivalent of sodium sulfite in water (2.2 times the mass of the monoester) is added and the solution stirred at 75° C. for 2 hours resulting in the product, lauryl disodium sulfomethylsuccinate as a 40% active soft white paste in water.

Lauryl disodium sulfomethylsuccinate has demonstrated superior foaming compared to other surfactants derived from 100% renewable carbon, such as alkyl polyglycosides and sodium lauryl sulfate. Lauryl disodium sulfomethylsuccinate is less irritating than sodium lauryl sulfate, is free of 1,4 dioxanes, sulfates, nitrosamines and salt, and can be easily formulated into different compositions as a surfactant to improve foaming.

In another aspect, the invention provides sulfomethylsuccinates of the following general structure:

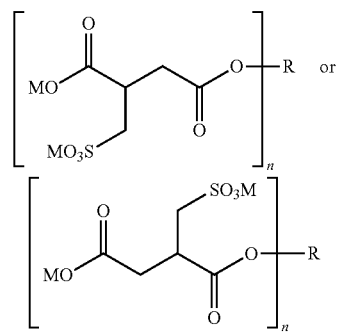

wherein R is derived from hydroxyl-containing compound. R may be an alkyl, alkenyl, alkynyl, alkoxylated alkyl, cycloalkyl, cycloalkenyl, cycloalkynyl, branched alkyl, branched alkenyl, branched alkynyl, branched alkoxylated alkyl, aromatic, substituted alkyl aromatic, substituted alkenyl aromatic or substituted alkoxylated aromatic group; each M is a cation, hydrogen, amine or ammonium salt, or a combination thereof, and n is from 1 to about 6.

In one embodiment, R comprises an alkyl group or an alkoxylated alkyl group. R can be derived from at least one hydroxyl-containing compound, such as an alcohol. As used herein, the term "hydroxyl-containing compound" refers generally to a compound that contains at least one hydroxyl ("OH") group. The R group of the hydroxyl-containing compound used to make the alkyl sulfomethylsuccinates of the present invention can be straight, branched, saturated, or unsaturated, and can be derived from natural or synthetic feed stocks. The alkyl group or alkoxylated alkyl group can optionally include from about 1 to about 22, alternatively from about 6 to about 18, alternatively from about 12 to about 18, alternatively from about 12 to about 14 carbon atoms. The hydroxyl-containing compound optionally contains at least one primary hydroxyl group. Optionally the hydroxyl-containing compounds are substantially free of secondary or tertiary hydroxyl groups. In accordance with some embodiments, the hydroxyl-containing compounds are primary fatty alcohols, for example, $C_{12}$-$C_{14}$ fatty alcohols in making one or more of the alkyl sulfomethylsuccinates of the present invention.

It has also been found that fatty alcohols, in particular $C_{12}$ or $C_{14}$ or $C_{12}/C_{14}$ alcohols, can provide R groups for alkyl sulfomethylsuccinates exhibiting improved and desired foaming, detergency, skin feel, and/or physical properties (e.g., viscosity building, solubility, and formulatability) for use in, for example, personal care, home care, and other cleansing applications. Although not intending to be bound by any particular theory, it is believed that $C_{12}/C_{14}$ sulfomethylsuccinates of the present invention can provide the best overall performance for at least some end-use applications (e.g., body washes, shampoos, etc.). It is also believed that an alkyl sulfomethylsuccinate made from $C_{16}$ or $C_{16}/C_{18}$ can produce a better skin feel, but less foam, for example. When lower alcohols are used, the resulting alkyl sulfomethylsuccinates can still provide good foaming performance, improved solubility, but their viscosity building properties may be worse than $C_{12}/C_{14}$ sulfomethylsuccinates. Examples of suitable fatty alcohols include lauryl alcohol, stearyl or coconut derived alcohol.

In addition, it is preferable that no solvent is used in the processes of the present invention to make the desired alkyl sulfomethylsuccinates. It is an object of the present invention to eliminate the use of a solvent in the reaction process for producing alkyl sulfomethylsuccinates for at least some applications, such as personal care applications. However, typically, a solvent-free process can be difficult to operate because of viscosity or product distribution concerns. The alkyl sulfomethylsuccinate products produced by the processes of the present invention may contain more than about 50%, more than about 60%, more than about 70%, more than about 80% or more than about 90% by weight of at least one alkyl sulfomethylsuccinate as described herein.

In some embodiments, the alkoxylated alkyl group R of the hydroxyl-containing compound are alkoxylated alcohols, for example, alcohols that are ethoxylated, propoxylated or both. Alternatively, the hydroxyl-containing compounds can be alkoxylated in situ when synthesizing the alkyl itaconate. Optionally, preformed alkoxylated hydroxyl-containing compounds can be used. For example, ethoxylated lauryl alcohols can be used to produce ethoxylated lauryl sulfomethylsuccinates containing a specific amount of ethoxy (EO) groups per mole of the sulfomethylsuccinate (e.g., typically from about 1 to about 12 ethoxy groups per mole of the sulfomethylsuccinate). Alkoxylation can change, among other things, the polarity of an alkyl sulfomethylsuccinate molecule, which can make the resulting sulfomethylsuccinate molecule more water soluble and affect its hydrophilic/lipophilic balance (HLB). It can also affect the packing of a surfactant during aqueous micellar formation. Alkoxylation can further affect the wetting ability, cloud point, and other surfactant properties of the alkyl sulfomethylsuccinate. It is also believed that alkoxylation can affect the ability to form a microemulsion with lower surfactant actives, change in clarity and stability. The cleaning performance of a sulfomethylsuccinate surfactant may also be affected, and the ability to tailor properties of the surfactant is increased.

In certain embodiments, the R group can be derived from diols or other polyols containing at least one primary OH. Optionally, the R group can be derived from a polyol containing two or more primary hydroxyl groups (OH's). For example, when a compound containing two primary hydroxyl groups is used as the bridging molecule the sulfomethylsuccinate in accordance with some embodiments of the present invention can be represented by the following general structure:

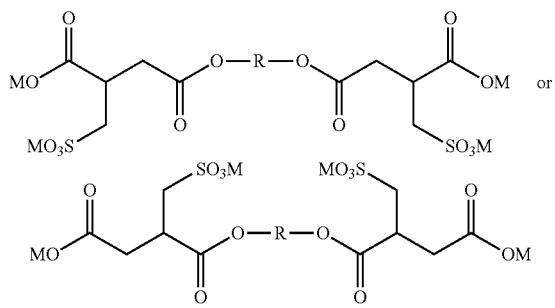

In accordance with some embodiments, the R group in the above formula can be an alkyl group or an alkoxylated alkyl group that is linear, branched, saturated or unsaturated and may contain from 1 to about 24 carbon atoms, optionally from 2 to about 22 carbon atoms, for example, from about 6 to about 18 carbon atoms, and in certain embodiments, from about 10 to about 14 carbon atoms. M may be as described elsewhere herein.

It has been discovered that the processes of the presently described invention can result in product yields in excess of about 50% of the targeted alkyl sulfomethylsuccinate, and the purity of alkyl sulfomethylsuccinate(s) in the product mixture without further purification can reach about 90% or more, alternatively about 95% or more, based on the total weight of the product mixture. The amount of either the alkyl itaconate or the remaining alcohol may be less than about 30% based on the total weight of the product mixture. In some embodiments, the amount of alkyl itaconate or fatty alcohol is less than about 20%. For example, the amount of alkyl itaconate or fatty alcohol may be less than about 10%, and in some cases, the amount of alkyl itaconate or fatty alcohol is less than about 5%. The mixture can be used in personal care and other applications. The residual impurities can be left in, or removed by, for example, water washing, adsorption onto basic alumina or silica media, or via neutralization with a base. In accordance with at another embodiment of the present invention, the hydroxyl-containing compound can be a fatty alcohol or alkoxylated fatty alcohol.

At least some alkyl sulfomethylsuccinate compounds of the present invention are clear, colorless liquids at room temperature, and are nitrogen free, salt-free, and sulfate-free. Optionally, the alkyl sulfomethylsuccinates can be formulated into products using a cold-mix process. At least some alkyl sulfomethylsuccinates of the present invention can provide improved performance (e.g., better skin feel, improved skin moisturization, enhanced foaming, modified viscosity building properties, improved mildness, improved hair color wash fastness, etc.), improved cost structure (e.g., by reducing the amount of total actives in formulated products), and/or improved stability. Further, at least some of the alkyl sulfomethylsuccinates are as mild or milder than conventional surfactants such as alkyl sulfates, alkyl ethersulfate, alkyl sarcosinates, methyl ester sulfonates, or alkyl sulfosuccinates. The alkyl sulfomethylsuccinates of the present invention may also be used as emulsifiers or skin feel agents. For household, industrial and institutional cleaning products, at least some of the alkyl sulfomethylsuccinates of the present invention can provide improved properties because of their surfactant properties as described above. In addition, they also can improve, for example, wetting or other surface modification, and aid in emulsification or dispersion of soils/particulates or other formulation ingredients.

At least some alkyl sulfomethelsuccinates of the present invention can be used as rheological modifiers to increase or reduce the viscosity of a composition as desired. It has been found that comparable viscosity values of a surfactant system can be achieved with significantly lower levels of electrolytes (e.g., NaCl) by incorporating at least one alkyl sulfomethylsuccinate of the present invention into the surfactant system. On the other hand, it has also been found that by incorporating at least one alkyl sulfomethylsuccinate of the present invention in another surfactant formulation, the viscosity can be significantly reduced.

Examples of cleaning formulations and other applications that can contain the alkyl sulfomethylsuccinates of the present invention include, but are not limited to:

Personal cleansing products (such as bar soap, bubble bath, shampoo, body wash, facial cleanser, hand soap, shower gel, wipes, baby cleansing products, etc.);

Creams/lotions (such as lotion with sun-screen protection, anti-aging creams (AHA, BHA), lightening lotion, brightening lotion, lotion with anti-oxidants, tanning lotion, etc.);

Cosmetic products (such as make-up, mascara, lipstick, etc.);

Hair treatment products (such as hair conditioners, hair spray, hair gel, etc.);

Home care or industrial or institutional products (heavy-duty detergents, light-duty detergents, fabric softeners, spot treatments, hard surface cleaners, degreasers and/or disinfectants such as those used in the kitchen for countertops, appliances, floors and walls, and bathroom cleaners and disinfectants such as those used for toilets, bath tubs, kitchen and bathroom sinks, showers, floors and walls, polishes, etc.);

Anti-perspirant/deodorants (solid, roll-on, etc.);

Enhanced oil recovery products (such as for wettability alteration);

Agriculture products (such as pesticidal, herbicidal, e.g., glyphosate, miticidal, formulations);

Solvent products (such as active solubilizers, pour point suppressors, flash point and polarity modifiers);

Gypsum products (such as foamers and wetters);

Paint and coating products (such as decorative paints, varnishes, cleaners, anti-graffiti formulations, etc.); and Emulsification products (such as skin creams, gels, semi-solids);

A formulated product such as a shampoo, optionally contains about 0.01% to about 95%, alternatively about 0.01% to about 80%, alternatively about 0.1% to about 60%, alternatively about 0.5% to about 40%, alternatively about 1% to about 20%, alternatively about 3% to about 15%, of the alkyl sulfomethylsuccinate of the present invention, based on the total weight of the product.

For example, a cleansing composition comprising the alkyl sulfomethylsuccinate of the present invention optionally further contains at least one or more other surfactants such as anionic, cationic, non-ionic, amphoteric, semi-polar non-ionic or zwitterionic surfactants, derivatives thereof, or mixtures thereof. These surfactants are known in the art, and are described in, for example, U.S. Pat. No. 3,929,678 (Laughlin et al.), which is incorporated herein by reference. Examples of useful cationic surfactants also include those described in U.S. Pat. No. 5,929,022 (Murphy) and U.S. Pat. No. 4,222,905 (Cockrell), both of which are incorporated herein by reference. In accordance with some embodiments, the one or more other surfactants in a cleansing composition can represent from about 0.1% to about 95%, alternatively from about 2% to about 70%, alternatively from about 2% to about 30%, alternatively from about 3% to about 10%, by weight of the cleansing composition.

Examples of nonionic surfactants for use with the present invention include, but are not limited to, alkyl phenol ethoxylates, alcohol alkoxylates, propyl glycols, lauryl lactyl lactate, alkyl polyglycerol esters, alkyl alcohol, alkyl mono, di or triglyceride, alkyl dimethyl or alkyl amidopropyl dimethyl amine oxides, alkanolamides, alkyl polyglycoside, ethoxylated alkanolamides, and mixtures thereof.

Examples of anionic surfactants include, but are not limited to, alcohol sulfates, alcohol alkoxy sulfates, alkylbenzene sulfonates, alpha olefin sulfonates, alpha sulfo methyl or ethyl esters of C8 through C18 fatty acids (mono end/or di-salts), sulfosuccinates, glutamates, sarcosinates, sulfoacetates, isethionates, paraffin sulfonates, acyl lactylates, alkyl amphoacetates, alkyl ether carboxylates, alkyl poly glucoside carboxylates, alkyl taurates, lauryl glucose carboxylates, alkyl glutamates, alkyl carboxylic acid, or derivatives thereof, and/or combinations thereof. Optionally, the alkyl groups in the anionic surfactants have from about 8 to about 18 carbon atoms. The counter ions for the anionic surfactants can be, for example, sodium, potassium, triethanol amine, monoethanol amine, ammonia, magnesium, etc. For laundry and liquid dishwashing detergents, preferred anionic surfactants include, but are not limited to, alkylbenzene sulfonates, alkyl ethoxy sulfates, and alpha sulfo methyl ester $C_{12-18}$. For hard surface cleansing compositions, preferred anionic surfactants include, for example, alkylbenzene sulfonates, alcohol sulfates, and alkyl ethoxy sulfates.

Examples of amphoteric surfactants include, but are not limited to, sultaines, betaines, alkyl dimethyl or alkyl amidopropyl dimethyl betaines, alkyl dimethyl or alkyl amidopropyl dimethyl amine oxides, mono- or di-sodium alkyl ampho (mono- or di)acetates; proprionates and mixtures thereof. For liquid dishwashing detergents, preferred amphoteric surfactants include, for example, betaines and amine oxides. For laundry detergents and hard surface cleansing compositions, preferred amphoteric surfactants include, for example, amine oxides.

Examples of quaternary ammonium compounds (quats) that can be used in combination with the alkyl sulfomethylsuccinates of the present invention include, but are not limited to, dialkyl dimethyl ammonium chlorides, alkyl dimethyl benzyl/ethyl benzyl ammonium chlorides, alkyl dimethyl benzyl ammonium chlorides, and mixtures thereof. When the products containing the alkyl sulfomethylsuccinates of the present invention are hard surface disinfectants or sanitizers, the quaternary ammonium compounds are optionally registered antimicrobial products, and should be used at an effective amount to kill the targeted organisms.

Anionic, non-ionic, semi-polar non-ionic and zwitterionic surfactants are preferred surfactants to be used in combination with the alkyl sulfomethylsuccinates of the present invention for cleansing compositions. Useful anionic surfactants specifically include those described in U.S. Pat. No. 3,929,678 (Laughlin et an and those described in U.S. Pat. No. 4,199,483 (Jones), which are incorporated herein by reference.

When an alkyl sulfomethylsuccinate of the present invention is used in a personal care liquid cleansing composition in accordance with at least one embodiment of the present invention, the personal care liquid cleansing composition optionally comprises about 0.1% to about 95%, alternatively about 1% to about 70%, alternatively about 1% to about 30%, alternatively about 1% to about 10%, alternatively about 1% to about 5%, of other surfactants; and about 0.01% to about 95%, alternatively about 0.01% to about 80%, alternatively about 0.1% to about 60%, alternatively about 0.5% to about 40%, alternatively about 1% to about 20%, alternatively about 3% to about 15%, of the alkyl sulfomethylsuccinate of the present invention, based on the total weight of the product. The very low concentrations for the bottom ranges can be used, for example, when finger pump foamers are used as the packaging and delivery systems. It is known to those skilled in the art that finger pump foamers are very efficient packaging systems that can deliver excellent foam at very low surfactant concentrations. Production costs can be reduced with such delivery systems.

Examples of preferred cleansing systems for personal care applications are readily known to those skilled in the art and can include combinations of anionic surfactants and zwitterionic co-surfactants. U.S. Pat. No. 5,705,147 (Shapiro, et al.) incorporated herein by reference provides a detailed description of such surfactants used to prepare personal care cleansers. The alkyl sulfomethylsuccinates of the presently described invention, when incorporated in formulations containing mixtures of the surfactants described in U.S. Pat. No. 5,705,147 (Shapiro, et al.), for example, can provide enhancement in foam ability, flow-ability and viscosity modification.

A detergent composition comprising the alkyl sulfomethylsuccinate of the present invention optionally contains from about 0.01% to about 95%, alternatively about 0.01% to about 80%, alternatively about 0.1% to about 60%, alternatively about 0.5% to about 40%, alternatively about 1% to about 20%, alternatively about 3% to about 15%, of the alkyl sulfomethylsuccinate of the present invention, based on the total weight of the product.

For example, a heavy-duty or light-duty liquid detergent formulation of the present invention optionally contains at least one alkyl sulfomethylsuccinate of the invention as a co-surfactant in conjunction with surfactants. In such applications, the alkyl sulfomethylsuccinate(s) can be present in an amount of, for example, 0.1% to about 50% actives for a heavy-duty laundry formulation with or without enzyme; and in an amount of, for example, 0.1% or 50% for a light-duty laundry or hand dishwashing formulation, based upon the total weight of the formulation. Examples of suitable surfactants for use in such formulations can be anionic, cationic, amphoteric, semi-polar non-ionic and non-ionic and may include, but are not limited to, alkylbenzene sulfonate, sodium laureth sulfate (3 EO), sodium laureth sulfate (2 EO), and sodium methyl-2-sulfopalmitate/disodium 2-sulfopalmitate.

As another example, the alkyl sulfomethylsuccinate of the present invention can be used as a surfactant in ultra dish wash detergent formulations in amounts less than about 30% actives based upon the total formulation, such as, for example, as low as about 0.1% actives based upon the total formulation.

The alkyl sulfomethylsuccinates of the present invention can be used as primary, secondary or co-surfactants in compositions comprising different surfactants such as alkyl sulfates, alkyl ether sulfates, olefin sulfonates, alkyl benzene sulfonic acids, alkyl benzene sulfonates, and alkali metal, alkaline earth metal, amine and ammonium salts thereof. The alkyl sulfomethylsuccinates of the present invention can be used to substitute or in combination with conventional or new secondary surfactants such as amides, betaines, sultaines, and alkyl polyglucosides. Examples of other surfactants include, but are not limited to, sodium lauryl sulfate (SLS), sodium laureth sulfates (SLES), sodium coco sulfate, sodium lauryl glucose carboxylate, alkyl polyglucoside (APG), alkyl benzene sulfonate, sodium lauryl glucoside, ammonium laureth sulfates, triethanolamine lauryl sulfate, poly decyl glucoside carboxylate, derivatives thereof, and combinations thereof. Examples of secondary surfactants that can be substituted or in combination with the alkyl sulfomethylsuccinates of the present invention include, but are not limited to, cocamidopropyl betaine, acyl lactylates such as sodium lauroyl lactylate, amphoacetates such as sodium cocoamphoacetate, sulfosuccinates such as sodium di(2-ethylhexyl)sulfosuccinate, lauryl glucoside, sodium cocoyl glutamate, monoethanol and diethanol based amides such as cocamide monoethanolamide, derivatives thereof, and combinations thereof.

It has been found that the alkyl sulfomethylsuccinate or a mixture of alkyl sulfomethylsuccinates of the present invention (e.g., lauryl sulfomethylsuccinate) has a comparable critical micelle concentration (CMC) to typical anionic surfactants such as, and not limited to, sodium lauryl sulfate, sodium laureth sulfate, sarcostinates, methyl ester sulfonates and sulfosuccinates. For example, the lauryl sulfomethylsuccinate of the present invention possesses a critical micelle concentration (CMC) of about 90 mg/L, while dodecyl sulfosuccinate has a CMC of about 120 mg/L. Thus, without intending to be bound by any particular theory, it is believed that at least some of the alkyl sulfomethylsuccinates of the present invention can provide comparable detergency to conventional anionic surfactants.

In accordance with at least one embodiment of the present invention, an alkyl sulfomethylsuccinate or composition comprising an alkyl sulfomethylsuccinate in an aqueous system can further comprise a buffer to improve the high temperature stability of the composition. Such a buffer may comprise, for example but not limited to, a sufficient amount of citric acid/sodium citrate, succinic acid/sodium succinate, or a mixture thereof. Optionally, the buffer system should be provided in a sufficient amount to stabilize the pH of the resultant formulation for at least four weeks in a stability test at 50° C. The proper amount of the buffer needed can be determined by routine steps/tests known and appreciated by those skilled in the art, and is dependent on the level of alkyl sulfomethylsuccinate(s) and/or other actives used in the end-use formulation. Any surfactants and buffering agents suitable for personal care, home care, or industrial and institutional products can be used. Examples of buffering systems include, but are not limited to, a citric acid/sodium citrate buffer, a succinic acid/ammonium succinate buffer, sodium carbonate buffer, or a combination thereof. Without intending to be bound by any particular theory, it has been observed in the present invention that the high temperature stability of the composition can be extended by using a buffer. For cleansing applications, each surfactant system can have a different buffer system with a different concentration. The proper amount of the buffer needed can be determined by known testing appreciated by those skilled in the art, and is dependent on the level of sulfomethylsuccinate and other actives used in a formulation. In general, the level of the buffer can be in the range of from about 0% to about 3%, alternatively from about 0.1% to about 2%, alternatively from about 0.1% to about 0.5%, based on the weight of the formulation.

In addition to aqueous systems, the alkyl sulfomethylsuccinates of the present invention can also be formulated into a solid, a gel, or other forms of personal care products or other applications. For example, the alkyl sulfomethylsuccinates of the present invention can be added into soap bars as a surfactant. Compared to conventional surfactants for soap bars such as fatty acid soaps, at least some alkyl sulfomethylsuccinates of the present invention can exhibit improved foaming performance, In accordance with some embodiments of the present invention, a soap bar optionally comprises (1) about 0.01 to about 60% of the alkyl sulfomethylsuccinate of the present invention, (2) about 0 to about 50% of a synthetic surfactant, (3) about 0 to about 30% of at least one alpha sulfonated alkyl ester, at least one sulfonated fatty acid, or a mixture thereof, (4) about 30% to about 95% of a $C_6$-$C_{22}$ soap, (5) about 0.5% to about 30% of a $C_6$-$C_{22}$ fatty acid, (6) about 0.1% to about 5% of an electrolyte, (7) about 0.5% to about 15% of a polyhydric alcohol, and (8) about 3% to about 22% of water, all based on the total weight of the soap bar.

Alternatively, the soap bar can comprise: (1) about 1 to about 50% of the alkyl sulfomethylsuccinate of the present invention, (2) about 0 to about 20% of a synthetic surfactant, (3) about 0 to about 15% of at least one alpha sulfonated alkyl ester, at least one sulfonated fatty acid, or a mixture thereof, (4) about 30% to about 95% of a $C_6$-$C_{22}$ soap, (5) about 0.5% to about 10% of a $C_6$-$C_{22}$ fatty acid, (6) about 0.1% to about 3% of an electrolyte, (7) about 0.5% to about 10% of a polyhydric alcohol, and (8) about 3% to about 22% of water, all based on the total weight of the soap bar.

Alternatively, the soap bar can comprise: (1) about 25 to about 45% of the alkyl sulfomethylsuccinate of the present invention, (2) about 0 to about 10% of a synthetic surfactant, (3) about 0 to about 10% of at least one alpha sulfonated alkyl ester, at least one sulfonated fatty acid, or a mixture thereof, (4) about 30% to about 95% of a $C_6$-$C_{22}$ soap, (5) about 0.5% to about 5% of a $C_6$-$C_{22}$ fatty acid, (6) about 0.1% to about 2% of an electrolyte, (7) about 0.5% to about 6% of a polyhydric alcohol, and (8) about 3% to about 22% of water, all based on the total weight of the soap bar.

In accordance with at least one other embodiment, the one or more sulfomethylsuccinates of the present invention can be included in an all-purpose cleaner concentrate in an amount of, for example, from about 0.01% to about 50%, alternatively from about 0.1% to about 20% actives based on the total weight of the concentrate.

In accordance with at least one other embodiment, the one or more sulfomethylsuccinates of the present invention can be included in a ready-to-use cleaner in an amount of, for example, from about 0.01% to about 50%, alternatively about 0.1% to about 20% actives based on the total weight of the cleaner.

One or more sulfomethylsuccinates of the present invention can also be included in a glass cleaner in an amount of, for example, from about 0.01 to about 30% actives based on the total weight of the cleaner.

Further, one or more sulfomethylsuccinates of the present invention can be included in a bathroom cleaner in an amount of, for example, from about 0.01 to about 50% actives based on the total weight of the cleaner.

Moreover, one or more sulfomethylsuccinates of the present invention can also be included in a liquid scouring cleaner in an amount of, for example, from about 0.01 to about 50% actives based on the total weight of the cleaner.

One or more sulfomethylsuccinates of the present invention can also be included in a dishwashing powder or gel in an amount of for example, from about 0.01 to about 50% actives based on the total weight of the formulation.

One or more sulfomethylsuccinates of the present invention can also be added into a carpet traffic spotter in an amount of, for example, from about 0.1% to about 50% actives, based on the total weight of the composition.

One or more sulfomethylsuccinates of the present invention can also be added into an enhanced oil recovery formulation in an amount of, for example, from about 0.01% to about 50% actives, based on the total weight of the composition.

One or more sulfomethylsuccinates of the present invention can also be added into an agriculture formulation in an amount of, for example, from about 0.1% to about 30% actives, based on the total weight of the composition.

One or more sulfomethylsuccinates of the present invention can also be used as a solvent in an amount of, for example, from about 0.1% to about 99% actives, based on the total weight of the composition.

One or more sulfomethylsuccinates of the present invention can also be added into a gypsum formulation in an amount of, for example, from about 0.1% to about 50% actives, based on the total weight of the composition.

One or more sulfomethylsuccinates of the present invention can also be added into a paint formulation in an amount of, for example, from about 0.1% to about 50% actives, based on the total weight of the composition.

One or more sulfomethylsuccinates of the present invention can also be added into a coating formulation in an amount of, for example, from about 0.1% to about 50% actives, based on the total weight of the composition.

One or more sulfomethylsuccinates of the present invention can also be added into an emulsification formulation in an amount of, for example, from about 0.1% to about 90% actives, based on the total weight of the composition.

Various embodiments of sulfomethylsuccinates of the present invention can meet one or more of the above desired attributes, among others. That is, certain disclosed sulfomethylsuccinates are useful in personal care products because they are mild, salt-free, sulfate-free and made from 100% biorenewable carbon sources. Some disclosed sulfomethylsuccinates are liquid form at room temperature, have a non-nitrogen containing structure, can be used to formulate products using a cold process, and can perform as good as or better than existing surfactants. Household, industrial and institutional cleaning products that contain the sulfomethylsuccinates disclosed herein have the ability to emulsify, suspend or penetrate greasy or oily soils and suspend or disperse particulates, in order to clean surfaces; and then prevent the soils, grease, or particulates from re-depositing on the newly cleaned surfaces.

For example, an effective laundry detergent product should remove dirt from clothes and then keep the dirt in solution so that it is removed with the wash water instead of re-depositing of the washed clothes. The sulfomethylsuccinates described herein are also useful for controlling the foaming of different household, industrial and institutional products depending on the desired end-use applications. For example, a liquid manual dish washing detergent optionally has the ability to foam in the presence of soil that is being removed from dishware. Yet, for a laundry detergent or automated dish washing detergent for use in a high efficiency washing machine, low foam is desired to achieve the best cleaning and to avoid excess foaming to allow machine proper operation.

Other desirable properties of such consumer products include the ability to clarify the formulation and to improve stability. For hard surface cleaners, it is desirable to have the ability to wet various surface types and couple or suspend soils to leave the surface free from residue in the form of streaking and/or filming. Disclosed sulfomethylsuccinates can be incorporated into, for example, various compositions and used as surfactants, emulsifiers, skin feel agents, film formers, rheological modifiers, solvents, release agents, lubrication agents, conditioners, and dispersants, etc. Such compositions can be used in end-use applications including, but not limited to, personal care, as well as household and industrial and institutional cleaning products. They can also be used in oil field applications, gypsum foamers, paints and coatings, adhesives, or other applications requiring cold tolerance performance or winterization (e.g., applications requiring cold weather performance without the inclusion of additional volatile components).

Sulfomethylsuccinates disclosed herein are advantageous relative to other surfactants due to the avoidance of nitrosamine formation; they are less irritating to the skin than SLS, and they are non-corrosive to metal tanks.

The presently described invention and its advantages will be better understood by reference to the following examples. These examples are provided to describe specific embodiments of the present invention. By providing these specific examples, the applicants do not limit the scope and spirit of the present invention. It will be understood by those skilled in the art that the full scope of the presently described invention encompasses the subject matter defined by the claims appending this specification, and any alterations, modifications, or equivalents of those claims.

EXAMPLES

General Methods/Instrument Details

All reactions were carried out under an inert atmosphere of nitrogen using standard Schlenk techniques unless otherwise noted. Deuterated solvents were purchased from Cambridge Isotope Laboratories Inc. and used as received. Itaconic acid was obtained from Cargill Inc. and was used without any further purification. Lauryl alcohol (C1214N) was purchased from Kao Chemicals and used as received. All other chemicals were used as received and purchased from Fisher Scientific. $^1$H NMR and $^{13}$C{$^1$H} NMR spectra were recorded on a Jeol Eclipse 500 MHz FT-NMR spectrometer and referenced relative to TMS resonances in deuterated chloroform (CDCl$_3$) and to residual proton resonances in dimethylsulfoxide (DMSO). All chemical shifts are reported in parts per million (ppm).

Example 1

Preparation of Alkyl Sulfomethylsuccinate

Methane sulfonic acid (0.135 milliliter (mL), 2.1 micromole (umol)) was added via micropipette to dipropylene glycol dimethyl ether (DPGDME) (40.00 grams (g), 247 millimole (mmol)), and the resulting solution was stirred. Itaconic acid (20 g, 151 mmol) was added and the reaction heated to 150° C. under 250 mmHg vacuum. A Dean Stark trap and condenser allowed for water removal (2.7 g, 151 mmol). NMR testing indicated substantially complete conversion of the itaconic acid. Upon completion, the DPGDME solvent was removed in vacuo resulting in the product, itaconic anhydride.

Itaconic anhydride (17.27 g, 151 mmol) and primary fatty alcohol (Kao C1214N, 29.50 g 151 mmol) were combined and heated to 110° C. for 120 min. resulting in the product, β-Monolaurylitaconate. NMR testing indicated substantially complete conversion of the itaconic anhydride.

β-Monolaurylitaconate (43.46 g, 151 mmol), de-ionized water (98.36 mL) and sodium sulfite (19.27 g 152 mmol) were combined and heated to 70° C. for 180 min. resulting in about 39% w/w active product, disodium monolauryl sulfomethylsuccinate, in water. NMR testing indicated substantially complete conversion of the itaconate.

Example 2

Preparation of Alkyl Sulfomethylsuccinate Via Direct Esterification of Itaconic Acid Itaconic acid (100 g, 757 mmol), primary fatty alcohol (Kao C1214H, 147 g, 757 mmol) and para-toluene sulfonic acid (0.14 g, 0.8 mmol) were combined and heated to 150° G for 6 hrs. NMR testing indicated substantially complete conversion of the itaconic acid. The resulting product was alkyl itaconate.

Alkyl itaconate (43.46 g, 151 mmol), de-ionized water (98.36 mL) and sodium sulfite (19.27 g, 152 mmol) were combined and heated to 70° C. for 180 min. resulting in about 39% w/w active product, disodium laurylitaconate, in water. NMR testing indicated substantially complete conversion of the itaconate.

Example 3

Preparation of Alkoxy Sulfomethylsuccinate

Itaconic anhydride (0.5 g, 4 mmol) and 3 mole alcohol ethoxylate (1.45 g, 4 mmol) were combined and heated to 100° C. for 90 min. resulting in the product, alkoxy itaconate. NMR testing indicated substantially complete conversion of the itaconic anhydride.

Alkoxy itaconate (1.95 g, 4 mmol), de-ionized water (3.90 mL) and sodium sulfite (0.73 g, 5 mmol) were combined and heated to 70° C. for 18 hours resulting in about 39% w/w active product, disodium monoalkoxy sulfomethylsuccinate, in water. NMR testing indicated substantially complete conversion of the itaconate.

Example 4

Preparation of tetra sodium 2-sulfomethylsuccinic acid 4-[2-(2-sulfomethylsuccinic acid)-ethyl ester Itaconic anhydride (100 g, 892 mmol) and ethylene glycol (27.69 g, 448 mmol) were combined and heated to 100° C. for 90 min. resulting in the product, diitaconic ethyl ester. NMR testing indicated substantially complete conversion of the itaconic anhydride.

Diitaconic ethyl ester (155 g, 892 mmol) and sodium sulfite (236 g, 1.87 mol) were combined and heated to 70° C. for 18 hrs resulting in tetra sodium 2-sulfomethylsuccinic acid 4-[2-(2-sulfomethylsuccinic acid)-ethyl ester. NMR testing indicated substantially complete conversion of the diitaconate ethyl ester.

Table A provides trade names and description of various components used in exemplary compositions of the present technology.

TABLE A

| Trade Names and Abbreviations | |
|---|---|
| STEOL ® CS-230 (SLES-2) | Sodium Salt of $C_{12}$-$C_{14}$ Alkyl Ethoxy Sulfate with 2 moles Ethylene Oxide per mole of alcohol, available from Stepan Company, Northfield, Illinois. |
| AMPHOSOL ® CDB Special | Cetyl betaine, available from Stepan Company, Northfield, Illinois. |
| AMPHOSOL ® HCG | Cocoamidopropyl betaine, available from Stepan Company, Northfield, Illinois. |
| AMPHOSOL ® HCA | Cocoamidopropyl betaine, available from Stepan Company, Northfield, Illinois. |
| AMPHOSOL ® CS-50 | Cocamidopropyl hydroxysultaine, available from Stepan Company, Northfield, Illinois. |
| AMPHOSOL ® 1C | Sodium Cocoamphoacetate, available from Stepan Company, Northfield, Illinois. |
| STEPAN-MILD ® L3 | Lauryl Lactyl Lactate, available from Stepan Company, Northfield, Illinois. |
| STEPAN-MILD ® GCC | Glyceryl Caprylate/Caprate, available from Stepan Company, Northfield, Illinois. |
| DREWPOL ® 10-1-CC | Decaglyceryl Mono(caprylate/caprate), available from Stepan Company, Northfield, Illinois. |
| STEPANOL ® WA-EXTRA (SLS) | Sodium lauryl sulfate, available from Stepan Company, Northfield, Illinois. |
| Plantacare 818 UP | Alkylpolyglucosides, available from Cognis Corp, Cincinnati, Ohio |
| STEPAN ® SLL-FB | Sodium Lauroyl Lactylate, available from Stepan Company, Northfield, Illinois. |
| Hostapon CT | Sodium Cocoyl Methyl Taurate, available from Clariant, Charlotte, North Carolina. |
| Hostapon SCI-85C | Sodium cocoyl isethionate, available from Clariant, Charlotte, North Carolina. |
| NINOL ® COMF | Cocamide Monoethanol Amine (MEA), available from Stepan Company, Northfield, Illinois. |
| LANTHANOL ® LAL | sodium lauryl sulfoacetate, available from Stepan Company, Northfield, Illinois. |
| KELTROL RD | Xanthan gum, available from CP Kelco U.S., Inc. Atlanta, GA |

Solubility and Surface Activity Test Method:

The solubility test for disodium alkyl sulfomethylsuccinate was done in DI water and observed visually at room temperature. The test was done at two conditions, with and without pH adjustment. The pH was adjusted with citric acid to achieve desired pH range.

Surface activity was measured with a K12 Krüss tensiometer at 25° C. in deionized water. Automatic titration was used to determine the critical micelle concentration (CMC). No pH adjustment was made for the measurement.

The viscosity was measured with a Brookfield LVT viscometer using spindle number 3 or number 4 at speed 12 rpm at ambient temperature. The viscosity of some formulations was also determined with a Rheologist AR2000 rheometer (from TA instruments) using 4 cm cone-plate geometry at 25° C. and 1 1/s (reciprocal second) shear rate.

Cylinder Inversion Foam Test Method:
1. Prepare a 0.2% active sample solution in the 25° C. tap water.
2. Add 100.0 g of the 0.2% sample solution to a 500 ml graduated cylinder. Keep the foam to a minimum.
3. Add 2.0 g of castor oil to the graduated cylinder and stopper the cylinder.
4. Place the graduated cylinder in the mechanical shake foam machine. Invert cylinder 10 times.
5. Allow the foam to settle for 15 seconds. Record an initial reading of total foam height. Record foam height again after 5 minutes.

Human Panel Hand Washing Test Method:

The method was described in WO2006/034190A1 (Dong et al) and is incorporated herein by reference.

Salon Half-Head Test Method:

Comb dry hair and divide into 2 sections (half head). Thoroughly wet hair.

Using a disposable syringe, apply 4 ml of each shampoo, control on one side, experimental on the other side.

Wash each side using eight circular motions to work up foam.

Evaluate the control and experimental shampoo for foam volume, density, stability, and rinsability.

Rinse hair with tap water for 10 seconds. Repeat procedures 1-4 using 2 ml of each shampoo. Then rinse for 10 seconds.

Evaluate the control and experimental shampoo for foam volume, density, stability, and rinsability.

Using a plastic comb, after the second shampooing, evaluate the hair for detangling and wet comb ability properties.

Blow-dry the hair and evaluate for dry comb ability, static, body, and shine.

The performance of each composition was tested on a scale of 0 to 3 compared to the control, with 0 being equal performance, 1 being slightly better, 2 being noticeably better, and 3 being obviously better. The individual assessments of each panelist was then averaged and recorded for each composition tested.

Performance Evaluation

Each of the exemplary compositions, as well as any compositions labeled "control composition," were prepared in de-ionized water. Materials used in all examples are expressed in weight percentage of an active matter. The final pH of each composition was adjusted to between about 2 to about 13, optionally between about 3 to about 11 for general liquid cleansers. The pH may be about 4 to about 9 for personal care compositions, and optionally about 4.5 to about 7, for example about 5 to about 6 using solution of either sodium hydroxide or citric acid.

Examples 5-9 In Table 1 demonstrated the typical properties of disodium alkyl sulfomethylsuccinate (DSS) in solution. In general, the non ethoxylated disodium alkyl sulfomethylsuccinates have limited water solubility at neutral pH. The solubility decreases with the increase of alkyl chain length. However, it was unexpectedly found that the pH had significant influence on the solubility of DSS. With decreasing of pH, the solubility of DSS was increased significantly, Example 6 demonstrated the influence of pH on solubility.

In another aspect of the invention, it was found the ethoxylated disodium alkyl sulfomethylsuccinate (example 9) had much better solubility in water as compared to its counterpart of the non-ethoxylated material (example 6).

TABLE 1

Properties of Disodium Alkyl Sulfomethylsuccinate (DSS) Examples

| Agents | Example 5 | Example 6 | Example 7 | Example 8 | Example 9 |
| --- | --- | --- | --- | --- | --- |
| Alkyl chain Length | 10 | 12 | 14 | 16 | 12 |
| Number of EO | 0 | 0 | 0 | 0 | 3 |
| Solubility at pH > 6.5 | 3% | <1% | <1% | <1% | >12% |
| Solubility at pH < 5.5 | na | >15% | na | na | na |
| CMC (mg/L) | 100 | 90 | 51 | 184 | na |
| Minimum Surface Tension (mN/m) | 29.6 | 30.1 | 28.3 | 41.5 | na |
| Foam Volume, no oil at neutral pH (ml) | 270 | 220 | 228 | 158 | na |

Although the disodium alkyl sulfomethylsuccinates have limited water solubility at neutral pH, they have been demonstrated to be effective surface-active agents. Examples 5-8 demonstrated the formation of micelles at very low active concentration and had sufficient surface tension reduction.

Figure 2:
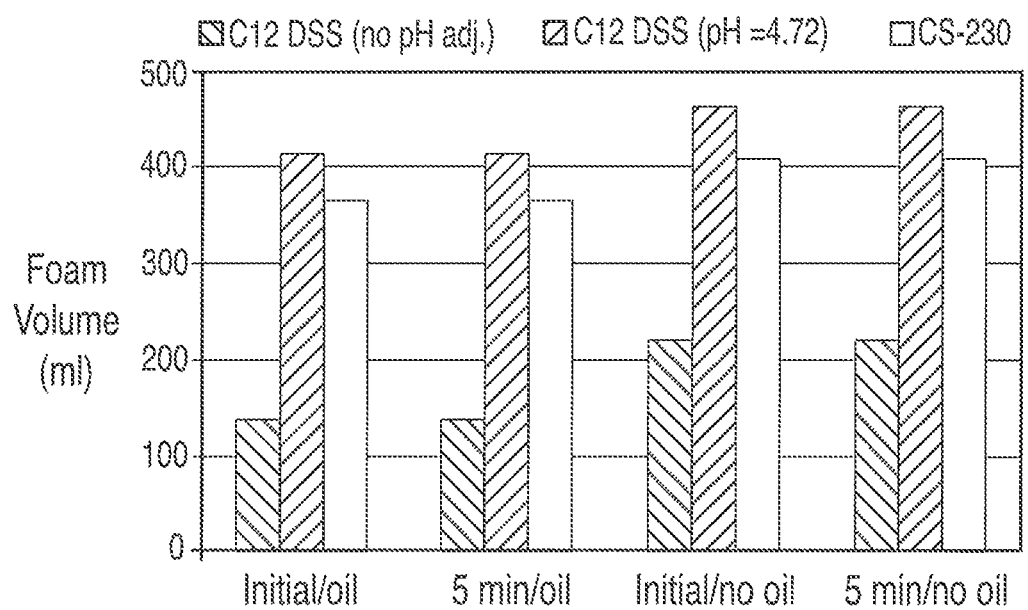
FIG. 2 is a bar chart showing foam volume results from cylinder inversion test at 0.2% active concentration with or without castor oil in Chicago tap water at 25° C.

Table 1 shows that all the disodium alkyl sulfomethylsuccinates have some foaming ability, however, the foam volume is not very high at the neutral pH conditions. It was surprisingly found that the foaming capability of disodium alkyl sulfomethylsuccinates improves significantly with the decrease of pH of alkyl sulfomethylsuccinate aqueous solution. For example, $C_{12}$ disodium sulfomethylsuccinate ($C_{12}$ DSS) was tested using cylinder inversion test, and results are given in FIG. 2. The foam volume of the material at pH 4.72 more than doubled to that at neutral pH. The foam volume is also higher than the most commonly used anionic surfactant SLES-2 under the same testing condition. The high foam ability and reasonable water solubility at lower pH makes disodium alkyl sulfomethylsuccinates strong candidates for use in high foaming cleansing products.

The potential of disodium alkyl sulfomethylsuccinates as foaming surfactants was evaluated in formulations with SLES-2 at 4/1 or 14/1 SLES-2/disodium alkyl sulfomethylsuccinates ratio. Formulation examples are given in Table 2. Most of the formulations are clear. All the DSS samples in combination with CS-230 (SLES-2) generated very good foam volume. Especially, C12 DSS and C14 DSS demonstrated significant improvement over the control formulation of CS-230/HCG at 4/1 ratio. The synergy between DSS and CS-230 in the foaming aspect is unexpected and very surprising.

TABLE 2

Cleansing Formulation Using DSS as Secondary Surfactants in combination with STEOL ® CS-230

|  | Example 10 Act % | Example 11 Active % | Example 12 Active % | Example 13 Active % | Example 14 Active % | Control |
|---|---|---|---|---|---|---|
| STEOL ® CS-230 | 12 | 14 | 12 | 12 | 12 | 12 |
| C16 DSS | 3 | 1 |  |  |  |  |
| C14 DSS |  |  | 3 |  |  |  |
| C12 DSS |  |  |  | 3 |  |  |
| C10 DSS |  |  |  |  | 3 |  |
| AMPHOSOL ® HCG |  |  |  |  |  | 3 |
| Water | q.s. to 100 | q.s. to 100 | q.s. to 100 | q.s. to 100 | q.s. to 100 | q.s. to 100 |
| Total Active | 15 | 15 | 15 | 15 | 15 | 15 |
| pH | 5.57 | 5.57 | 5.52 | 5.49 | 5.57 | 5.5 |
| Appearance | Cloudy | Clear | Clear | Clear | Clear | Clear |
| Foam Volume, no oil (ml) | 415 | 465 | 493 | 518 | 480 | 408 |
| Foam Volume, 2% Castor Oil (ml) | 330 | 350 | 400 | 413 | 380 | 275 |
| Viscosity @25° C., no salt (cps) | 1 | 1 | 1 | 1 | 1 | 1 |
| Viscosity @25° C., with 3% NaCl (cps) | 21,800 | 8,600 | 17,000 | 550 | 1 | 33,850 |

The superior foaming properties of disodium alkyl sulfomethylsuccinate also indicate that it can be used as a potential primary surfactant in high foaming cleansing products. Examples 15 to 22 in Table 3 demonstrate such application. Different surfactants or additives were used in combination with DSS. The pH of these formulations was adjusted with either citric acid or hydrochloric acid to pH of 4.5 to 6.5, which is the desired pH for personal care products. The foam property was evaluated with the cylinder inversion method.

TABLE 3

Cleansing Formulations Using C12 and C14 DSS as Primary Surfactants

|  | Example 15 % Act. | Example 16 % Act. | Example 17 % Act. | Example 18 % Act. | Example 19 % Act. | Example 20 % Act. | Example 21 % Act. | Example 22 % Act. |
|---|---|---|---|---|---|---|---|---|
| C12 DSS | 10 | 12 | 12 | 12 | 12 | 12 | 12 |  |
| C12-14 DSS |  |  |  |  |  |  |  | 10 |
| AMPHOSOL ® HCG |  |  | 3 | 2 |  |  |  |  |
| NINOL ® COMF |  |  |  | 1 |  |  |  |  |
| AMPHOSOL ® CDB Special | 5 | 3 |  |  |  |  |  |  |
| Stepan-Mild ® L3 |  |  |  |  | 1 | 1.5 |  |  |
| Stepan-Mild ® SLL-FB |  |  |  |  |  |  |  | 5 |
| Stepan-Mild ® GCC |  |  |  |  | 2 | 1.5 |  |  |
| LATHANOL ® LAL |  |  |  |  |  |  | 3 |  |
| Nacl | 0 | 0 | 2 | 2 | 2 | 1.5 | 1.5 | 1.5 |
| Citric acid (25%) | q.s. | q.s. | q.s. | q.s. | q.s. | q.s. | q.s. |  |
| HCl (35.5%) |  |  |  |  |  |  |  | q.s. |
| Keltrol RD |  |  |  |  | 0.2 | 0.2 |  |  |
| Water | q.s. to 100 | q.s. to 100 | q.s. to 100 | q.s. to 100 | q.s. to 100 | q.s. to 100 | q.s. to 100 | q.s. to 100 |
| Total active | 15 | 15 | 15 | 15 | 15 | 15 | 15 | 15 |
| pH | 4.98 | 4.96 | 5.00 | 5.03 | 5.38 | 5.34 | 5.19 | 5.44 |
| Appearance | Clear | Clear | Clear | Clear | Clear | hazy | Clear | Clear |
| Viscosity (cps) | 56,800 | 1,400 | 400 | 3,350 | 13,800 | 13,900 | 8,050 | 1,300 |
| Foam Volume, no oil (ml) | 400 | 390 | 430 | 405 | 380 | 375 | 420 | 375 |
| Foam Volume, 2% Castor oil (ml) | 295 | 323 | 390 | 400 | 375 | 325 | 375 | 360 |

The foaming performance was also evaluated using in-vivo panelist hand washing test following the procedures described previously. In the in-vivo test, other properties such as skin-feel and foam morphology were also evaluated. The results are presented in Table 4. Formulations 19 and 20 had significantly higher foam volume compared to the (CS-230/HCG) control formulation. It was also observed that it is easier to generate foam with the example formulations containing DSS. The foam from the example formulations of the present invention exhibited superior lubrication feel and bigger bubble size.

TABLE 4

Foam Evaluation Results Using Hand Wash Test

| Formulation | Foam Volume (ml) | Flash Foam Generation | Foam Feel | Bubble Size |
|---|---|---|---|---|
| Control (CS-230/HCG) | 107 | 0 | 0 | 0 |

TABLE 4-continued

Foam Evaluation Results Using Hand Wash Test

| Formulation | Foam Volume (ml) | Flash Foam Generation | Foam Feel | Bubble Size |
|---|---|---|---|---|
| Example 19 | 255 | 1.3 | 0.3 | 0.3 |
| Example 20 | 193 | 1.0 | 0.3 | 0.3 |

Formulation Examples 19 and 20 were also evaluated as a shampoo using salon half-head test on 3 panelists. These two formulations were compared against the control formulation in Table 2. The results demonstrated these two all natural sulfate-free formulations performed equal to the most commonly used surfactant system in shampoo application.

TABLE 5

Half-Head Salon Test Results for the Example Formulations Compared to the Control formulation

|  | Control | Example 19 | Control | Example 20 |
|---|---|---|---|---|
| First Application |  |  |  |  |
| flash foam | 0 | 0 | 0 | 0 |
| volume | 0 | 0 | 0 | 0 |
| stability | 0 | 0 | 0 | 0 |
| density | 0 | 0 | 0 | 0 |
| rinsability | 0 | 0 | 0 | 0 |
| Second Application |  |  |  |  |
| flash foam | 0 | 0 | 0 | 0 |
| volume | 0.3 | 0 | 0 | 0.3 |
| stability | 0 | 0 | 0 | 0 |
| density | 0 | 0 | 0 | 0 |
| rinsability | 0 | 0 | 0 | 0 |
| After Shampoo Condition |  |  |  |  |
| detangling | 0 | 0 | 0 | 0 |
| wet comb-ability | 0 | 0 | 0 | 0 |
| dry comb-ability | 0 | 0 | 0 | 0 |
| absence of static | 0 | 0 | 0 | 0 |
| body shine | 0 | 0 | 0 | 0 |

Yet, in another aspect of the present invention, alkyl sulfomethylsuccinates can be used as a co-surfactant or additive in a liquid cleansing composition. In such cases, alkyl sulfomethylsuccinates will help to improve the foaming, mildness, skin feel, rheology, hair color care, conditioning or other aspects of the formulation. Examples 23 to 32 in Table 6 demonstrated especially the foam improvement for formulations with alkyl sulfomethylsuccinates.

Each pair of the formulations had the same total active concentration and tested at the same conditions. One of the formulation contained disodium C12 sulfomethylsuccinate and the other one did not. The formulations comprising DSS had significantly higher foam volume compared to the one that did not have any DSS. The foam volume improved from about 20% to about 60% in general. The amount of DSS varies in these formulations. Example 29 contains only 1% of DSS. Yet, this formulation had 435 ml of foam verses Example 30 which had 300 ml of foam. The effectiveness of DSS on the improvement of foaming is clearly shown in these examples.

The examples in Table 6 also demonstrated that DSS worked effectively with variety of ingredients, including anionic, nonionic and cationic materials, functional materials and additives.

It has been noticed that the viscosity of some of the formulations depends on the composition and the pH of the formulation. Lower pH favors higher viscosity. However, in some cases it's difficult to build viscosity higher than 3,000 cps in a desired pH range by just using salt, such as sodium chloride. Polymeric thickening agent such as xanthan gum, hydroxylmethyl cellulose can be used to increase the viscosity of such compositions. Suitable polymeric rheological modifiers for use with the present technology can be polymers or copolymers, and can be in anionic, nonionic, amphoteric or cationic forms. Some examples of polymeric additives of the present technology include, but are not limited to, polyacrylic acids and the salts thereof, polyacrylates, polyacrylamides, copolymers acrylate of and acrylamide, copolymers of acrylate and hydroxyester acrylate, polyvinyl alcohols, polyethylene glycols, polyvinylacetates, polyvinyl pyrrolidones, hydroxylethyl cellulose, hydroxylmethyl cellulose, modified starches, modified xanthan pyrrogum, cationic cellulose, cationic starches, modified guar gum, copolymers of vinyl lidone and dimethylaminoethylmethacrylate, copolymers of vinyl pyr-

TABLE 6

Formulations Comprising DSS Compared to Those without DSS

|  | Example 23 Act. % | Example 24 Act. % | Example 25 Act. % | Example 26 Act. % | Example 27 Act. % | Example 28 Act. % | Example 29 Act. % | Example 30 Act. % | Example 31 Act. % | Example 32 Act. % |
|---|---|---|---|---|---|---|---|---|---|---|
| C12 DSS | 6 |  | 6 |  | 6 |  | 1 |  | 6 |  |
| STEPANOL ® WA-EXTRA |  |  |  |  | 3 | 9 | 9 | 9 |  |  |
| DREWPOL ® 10-1 CC |  |  | 6 | 12 |  |  |  |  |  |  |
| Plantacare 818UP | 6 | 12 |  |  |  |  |  |  |  |  |
| NINOL ® COMF | 3 | 3 |  |  |  |  |  |  |  |  |
| Hostapon CT |  |  |  |  |  |  |  |  |  | 6 |
| AMPHOSOL ® CS-50 |  |  |  |  |  |  |  |  | 4 | 4 |
| AMPHOSOL ® 1C |  |  |  |  |  |  |  |  | 3 | 3 |
| AMPHOSOL ® HCA |  |  | 3 | 3 | 6 | 6 |  |  |  |  |
| AMPHOSOL ® HCG |  |  |  |  |  |  | 2.5 | 2.5 |  |  |
| Hostapon SCI-85C |  |  |  |  |  |  |  | 1 |  |  |
| Glycerine |  |  |  |  | 2 | 2 | 1 | 1 | 2 | 2 |
| Polyquaterium-10 |  |  |  |  | 0.25 | 0.25 |  |  |  |  |
| NaCl |  |  |  |  |  |  |  |  | 1.5 | 1.5 |
| Citric acid (25%) | q.s. | q.s. | q.s. | q.s. | q.s. | q.s. | q.s. | q.s. | q.s. | q.s. |
| Water | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 |
| pH | 5.69 | 5.7 | 5.71 | 5.65 | 5.44 | 5.17 | 5.37 | 5.23 | 5.35 | 5.31 |
| Total Surfactant Active | 15 | 15 | 15 | 15 | 15 | 15 | 12.5 | 12.5 | 13 | 13 |
| Viscosity @25° C., cps | 1 | 170 | 1 | 1 | 17850 | 27,650 | 14,150 | 6,690 | 8,040 | 870 |
| Foam Volume, no oil (ml) | 325 | 205 | 375 | 300 | 450 | 320 | 435 | 300 | 440 | 300 |

The examples in Table 6 should be compared in pairs. For example. Example 23 should be compared to Example 24, and Example 25 should be compared to Example 26, and etc.

rolidone and vinyl acetate, copolymers of carboxylated vinyl acetate, polyethylene glycol, polyethylene glycol esters, derivatives thereof, and combinations thereof.

The present invention is now described in such full, clear, concise and exact terms as to enable any person skilled in the art to which it pertains, to practice the same. It is to be understood that the foregoing describes preferred embodiments of the invention and that modifications may be made therein without departing from the spirit or scope of the present invention as set forth in the appended claims.

What is claimed is:

1. An alkyl sulfomethylsuccinate of the formula:

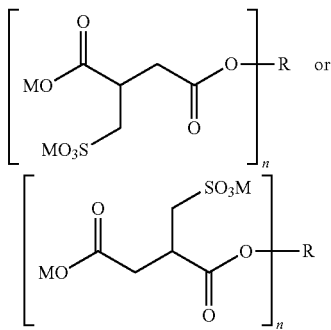

wherein R is an alkyl or alkoxylated alkyl group; M is an alkali metal, hydrogen, alkaline earth metal, ammonium or combinations thereof; and n is from 1 to 6.

2. The alkyl sulfomethylsuccinate of claim 1, wherein R is a $C_1$ to $C_{24}$ alkyl or alkoxylated alkyl group.

3. The alkyl sulfomethylsuccinate of claim 1, wherein R is a $C_6$ to $C_{18}$ alkyl or alkoxylated alkyl group.

4. The alkyl sulfomethylsuccinate of claim 1, wherein R is a $C_{12}$ to $C_{14}$ alkyl or alkoxylated alkyl group.

5. The alkyl sulfomethylsuccinate of claim 1, wherein M is sodium, hydrogen, or a mixture thereof.

6. The alkyl sulfomethylsuccinate of claim 5, wherein n is 1 or 2.

7. A process for making an alkyl sulfomethylsuccinate which comprises the steps of:
   (i) reacting itaconic anhydride with an alcohol of the general formula ROH to yield an itaconate ester, wherein R is an alkyl or alkoxylated alkyl group; and
   (ii) reacting the itaconate ester with a sulfonating agent to produce a sulfomethylsuccinate with the general formula:

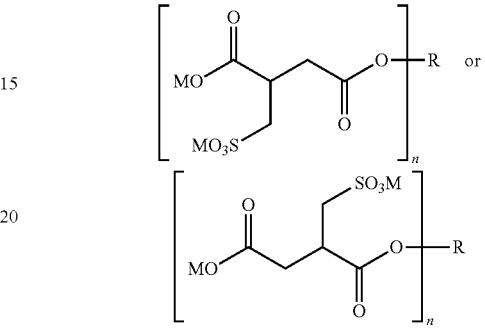

wherein M is an alkali metal, hydrogen, alkaline earth metal, ammonium, or a combination thereof; and n is from 1 to 6.

8. A personal cleansing product, a cream or lotion, a cosmetic product, a hair treatment product, a home care or industrial or institutional product, an anti-perspirant or deodorant, an enhanced oil recovery product, an agricultural product, a solvent product, a gypsum product, a paint or coating product, or an emulsification product comprising the alkyl sulfosuccinate of claim 1.

* * * * *